United States Patent [19]
Barenholz et al.

[11] Patent Number: 6,156,337
[45] Date of Patent: *Dec. 5, 2000

[54] METHOD FOR HIGH LOADING OF VESICLES WITH BIOPOLYMERIC SUBSTANCES

[75] Inventors: Yechezkel Barenholz, Jerusalem; Israel Nur, Tel Aviv; Lilianne K. Bar, Rehovot; Dvorah Diminsky, Jerusalem; Moshe Baru, Pardes-Hanna, all of Israel

[73] Assignee: Opperbas Holding B.V., Amsterdam Zuidoost, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/709,679

[22] Filed: Sep. 9, 1996

Related U.S. Application Data

[63] Continuation of application No. 08/591,538, filed as application No. PCT/EP94/02243, Jul. 8, 1994, abandoned.

[51] Int. Cl.[7] .......................... A61K 9/127; A61K 9/133
[52] U.S. Cl. .................. 424/450; 424/94.3; 424/812; 436/829; 935/54; 264/4.1; 264/4.3
[58] Field of Search .................... 424/450, 94.3, 424/812, 1.21, 9.321, 9.51; 264/4.1, 4.3; 436/829; 935/54

[56] References Cited

U.S. PATENT DOCUMENTS

| | | | |
|---|---|---|---|
| 4,235,871 | 11/1980 | Papahadjopoulos | 424/450 |
| 4,348,384 | 9/1982 | Horikoshi | 424/101 |
| 4,370,349 | 1/1983 | Evans | 424/450 |
| 4,877,561 | 10/1989 | Iga | 264/4.3 |
| 5,230,899 | 7/1993 | Park | 424/450 |
| 5,362,442 | 11/1994 | Kent | 422/22 |

FOREIGN PATENT DOCUMENTS

| | | |
|---|---|---|
| 2002319 | 2/1979 | United Kingdom . |
| 2135647 | 9/1984 | United Kingdom . |

*Primary Examiner*—Gollamudi S. Kishore
*Attorney, Agent, or Firm*—Jacobson, Price, Holman & Stern, PLLC

[57] ABSTRACT

A method for loading liposomes with biopolymeric substances functional in humans involves combining a physiologically compatible solution of the biopolymeric substances with one or more dry, liposome-forming lipids, effecting a lipid-containing fraction, combining the lipid-containing fraction with an organic solvent, effecting an organic solvent fraction, and drying the organic solvent fraction, which effects a dry fraction of liposomes loaded with the biopolymeric substances.

36 Claims, 8 Drawing Sheets

METHOD D

* - Small unilamellar vesicles

METHOD E

A METHOD OF PREPARING LIPOSOMES CONTAINING ACTIVE FACTOR (OR AGENT) BASED ON CO-LYOPHILIZATION OF LIPIDS AND AGENT (METHOD IV)

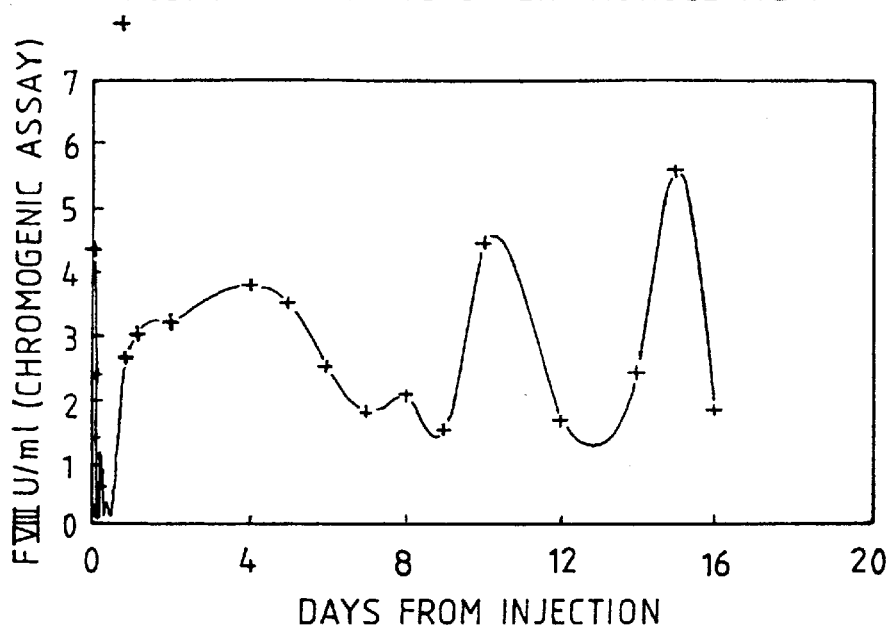
FIG.8 PHARMACOKINETICS IN FEMALE DOG
INJECTION: 900 UNITS OF LIP-MONOCLATE P
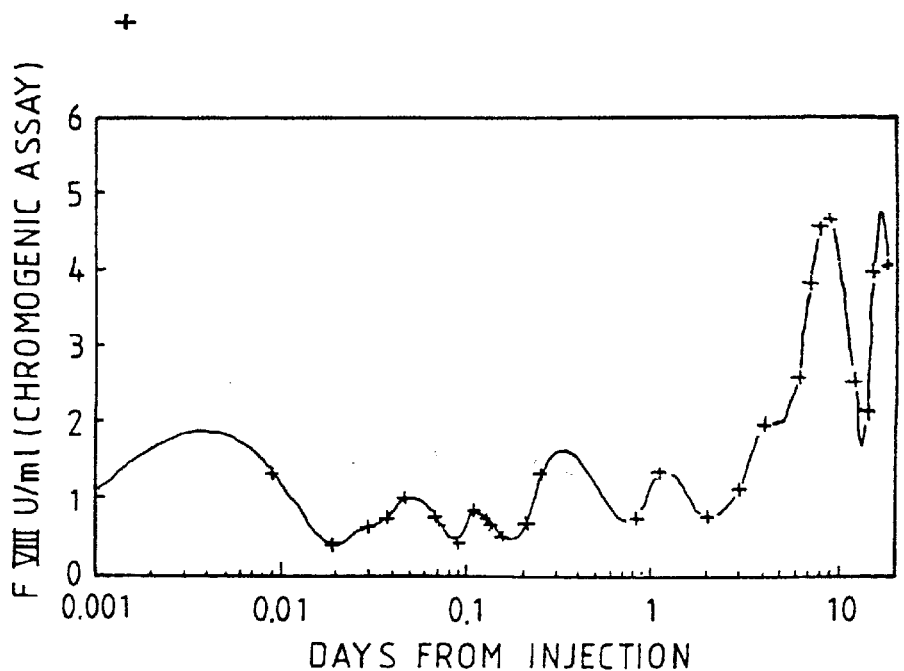
FIG.9 PHARMACOKINETICS IN MALE DOG
INJECTION: 900 UNITS OF LIP-octavi

METHOD FOR HIGH LOADING OF VESICLES WITH BIOPOLYMERIC SUBSTANCES

This is a continuation of application Ser. No. 08/591,538, filed Feb. 6, 1996, abandoned which is a 371 of PCT/EP94/02243 filed Jul. 8, 1994.

The invention is related with a high loading of vesicles with biopolymeric substances functional in human biochemical or physiological systems, derived from any source, said substances preferably are enzymes, growth factors, cytokines, proenzymes, co-factors, submicron-particles such as virions, ribosomes, hepatitis B surface antigen, vaccines, oligo- and polynucleotides, antibodies and/or antigenes, said vesicles formed by amphiphatic substances comprising the steps of formulation of substances obtainable by the method of the invention having an improved amount of effective substances loaded in the vesicles, a medicament comprising the formulation of the invention and a method of treating diseases by administering an effective amount of the medicament of the invention.

Several attempts have been tried to use lipid vesicles formed by natural or synthetic phospholipids as vehicles for the administration of effective substances.

Grey, A. and Morgan, J. report that liposomes were first described nearly a quarter of a century ago and have been useful models for studying the physical chemistry of lipid bilayers and the biology of the cell membrane. It was also realised that they might be used as vehicles for the delivery of drugs but clinical application have been slow to emerge. Proposed clinical uses have included vaccine adjuvancy, gene transfer and diagnostic imaging but the major effort has been in the development of liposomes as targetable drug carriers in the treatment of malignancy. Although based on good in vitro data and animal studies, the strategies have been mostly impractical due to the predominant but unwanted uptake by the reticuloendothelial system and the limited extent of extravasation. The same features have nonetheless been turned to advantage in the case of amphotericin B which has recently become the first liposomally formulated agent to be licensed for parenteral use. Liposomal doxorubicin is currently also being evaluated in clinical trials. The early evidence suggests that while liposomal encapsulation may not greatly enhance their efficacy the toxicity of these agents is greatly attenuated (A. Gray, J. Morgan, "Liposomes in Haematology" in Blood Reviews, 1991, 5, 258–271).

Liposomes have been used in biological systems such as plasma extravascular space like reticuloendothelial system to more access celluar uptake of liposomes. Liposomes were loaded with amphotericin which is an effective but toxic antifungal. Antitumor agents like adriamycine have also be incorporated into liposomes. Vaccines and adjuvants as well as biological response modifiers like lymphocines and so on were studied in encapsulated form. Liposomes are discussed in field of a gene transfert as vehicles.

N. Sakuragawa et al. report in Thrombosis Research 38, 681–685, 1985, 1988 Clinical Hematology 29 (5) 655–661, that liposomes containing factor VIII have been prepared for oral administration to patients which are suffering from von Willebrand's disease. The encapsulation was carried out by dissolving the protein factor VIII concentrates in an aprotinin containing solution and transferred into lecithin coated flasks. After drying the flasks by rotation for 30 min under negative pressure liposomes were formed which entrapped factor VIII concentrates. The liposome solution was centrifuged yielding 40% of factor VIII entrapped in liposomes.

Another method for entrapment of drugs in liposomes is based on dehydration—rehydration. This is described by C. Kirby and G. Gregoriadis in Bio/Technology, November 1984, pages 979–984. In this preparation the entrapments can be increased by using additional lipid. Disclosed is the use of cholesterol as being of positive influence of the drug entrapment. Since cholesterol is involed in the pathobiochemistry of some disorders, administration of cholesterol containing vesicles is not harmless at all.

A drawback of the liposome preparation of prior art is, for example, the low encapsulation efficiency of the substances, which encapsulation efficiency is lower than 50%.

One object of the present invention is to provide an improved method for loading vesicles (liposomes) with biopolymeric substances such as pharmaceutically effective substances as enzymes, proenzymes, co-factors, antibodies or antigenes. A further object is to provide a formulation having a high content of effective substances loaded in a vesicle (liposome). Another object is to show the use of the formulation of the invention for treating and preventing diseases. It is desirable to achieve the improvement by avoiding harmful lipids in the liposomes structures.

Surprisingly, a method described in greater detail hereinbelow is able to improve the loading of the vesicles (liposomes). The term vesicle is a synonym of liposome or liposome vesicle.

Liposomes can be classified according to various parameters. For example, when size and number of lamellae (structural parameters) are used than three major types of liposomes have been described: Multilamellar vesicles (MLV), small unilamellar vescicles (SUV) and large unilamellar vesicles (LUV). MLV are the species which form spontaneously on hydration of dried phospholipids above their gel to liquid crystalline phase transition temperature (Tm). Their size is heterogenous and their structure resembles an onion skin of alternating, concentric aqueous and lipid layers.

SUV are formed from MLV by sonication and are single layered. They are the smallest species with a high surface-to-volume ratio and hence have the lowest capture volume of aqueous space to weight of lipid.

A third type of liposome LUV has a large aqueous compartment and a single (unilamellar) or only a few (oligolamellar) lipid layers.

Further details are disclosed in D. Lichtenberg and Y. Barenholz, Liposomes: Preparation, Characterization, and Preservation, in Methods of Biochemical Analysis, Vol. 33, pp. 337–462.

As used herein the term "loading" means any kind of interaction of the biopolymeric substances to be loaded, for example, an interaction such as encapsulation, adhesion (to the inner or outer wall of the vesicle) or embedding in the wall with or without extrusion of the biopolymeric substances.

As used herein, the term "liposome" is intended to include all spheres or vesicles of any amphiphatic compounds which may spontaneously or non-spontaneously vesiculate, for example phospholipids where at least one acyl group replaced by a complex phosphoric acid ester. The most of triacylglycerol is suitable and most common phospholipids for the present invention are the lecithines (also referred to as phosphatidylcholines (PC)), which are mixtures of the diglycerides of stearic, palmitic, and oleic acids linked to the choline ester of phosphoric acid. The lecithines are found in all animals and plants such as eggs, soybeans, and animal tissues (brain, heart, and the like) and can also be produced synthetically. The source of the phospholipid or its method of synthesis are not critical, any naturally occurring or synthetic phosphatide can be used.

Examples of specific phosphatides are L-α-(distearoyl) lecithin, L-α-(diapalmitoyl) lecithin, L-α-phosphatide acid, L-α-(dilauroyl)-phosphatidic acid, L-α(dimyristoyl) phosphatidic acid, L-α(dioleoyl)phosphatidic acid, DL-α (dipalmitoyl) phosphatidic acid, L-α(distearoyl) phosphatidic acid, and the various types of L-α-phosphatidylcholines prepared from brain, liver, egg yolk, heart, soybean and the like, or synthetically, and salts thereof. Other suitable modifications include the controlled peroxidation of the fatty acyl residue cross-linkers in the phosphatidylcholines (PC) and the zwitterionic amphiphates which form micelles by themselves or when mixed with the PCs such as alkyl analogues of PC.

The phospholipids can vary in purity and can also be hydrogenated either fully or partially. Hydrogenation reduces the level of unwanted peroxidation, and modifies and controls the gel to liquid/crystalline phase transition temperature ($T_m$) which effects packing and leakage.

The liposomes can be "tailored" to the requirements of any specific reservoir including various biological fluids, maintains their stability without aggregation or chromatographic separation, and remains well dispersed and suspended in the injected fluid. The fluidity in situ changes due to the composition, temperature, salinity, bivalent ions and presence of proteins. The liposome can be used with or without any other solvent or surfactant.

Another important consideration in the selection of phospholipid is the acyl chain composition thereof. Currently, it is preferred that it has an acyl chain composition which is characteristic, at least with respect to transition temperature ($T_m$) of the acyl chain components in egg or soybean PC, i. e., one chain saturated and one unsaturated or both being unsaturated. However, the possibility of using two saturated chains is not excluded.

The liposomes may contain other lipid components, as long as these do not induce instability and/or aggregation and/or chromatographic separation. This can be determined by routine experimentation.

A variety of methods for producing the modified liposomes which are unilamellar or multilamellar are known and available:

1. A thin film of the phospholipid is hydrated with an aqueous medium followed by mechanical shaking and/or ultrasonic irradition and/or extrusion through a suitable filter;

2. dissolution of the phospholipid in a suitable organic solvent, mixing with an aqueous medium followed by removal of the solvent;

3. use of gas above its critical point (i. e., freons and other gases such as $CO_2$ or mixtures of $CO_2$ and other gaseous hydrocarbons) or 4. Preparing lipid detergent mixed micelles then lowering the concentration of the detergents to a level below its critical concentration at which liposomes are formed (Lichtenberg, Barenholz, 1988).

In general, they produce liposomes with heterogeneous sizes from about 0.02 to 10 μm or greater. Since liposomes which are relatively small and well defined in size are preferred for use in the present invention, a second processing step defined as "liposome down sizing" is for reducing the size and size heterogeneity of liposome suspensions.

The liposome suspension may be sized to achieve a selective size distribution of vesicles in a size range less than about 5 μm and preferably to be ≦0.4 μm. Liposomes in this range can readily be sterilized by filtration through a suitable filter. Smaller vesicles also show less a tendency to aggregate on storage, thus reducing potentially serious blockage or plugging problems when the liposome is injected intravenously. Finally, liposomes which have been sized down to the submicron range show more uniform distribution.

Several techniques are available for reducing the sizes and size heterogeneity of liposomes, in a manner suitable for the present invention. Ultrasonic irradiation of a liposome suspension either by standard bath or probe sonication produces a progressive size reduction down to small unilamellar vesicles (SUVs) between 0.02 and 0.08 μm in size. Homogenization is another method which relies on shearing energy to fragment large liposomes into smaller ones. In a typical homogenization procedure the liposome suspension is recirculated through a standard emulsion homogenizer until selected liposome sizes, typically between about 0.1 and 0.5 μm are observed. In both methods, the particle size distribution can be monitored by conventional laser-beam particle size determination.

Extrusion of liposomes through a small-pore polycarbonate filter or equivalent membrane is also an effective method for reducing liposome sizes down to a relatively well-defined size distribution whose average is in the range between about 0.02 and 5 μm, depending on the pore size of the membrane. Typically, the suspension is cycled through one or two stacked membranes several times until the desired liposome size distribution is achieved. The liposome may be extruded through successively smaller pore membranes, to achieve a gradual reduction in lipsome size.

Centrifugation and molecular sieve chromatography are other methods which are available for producing a liposome suspension with particle sizes below a selected threshold less than 1 μm. These two respective methods involve preferential removal of large liposomes, rather than conversion of large particles to smaller ones. Liposome yields are correspondingly reduced.

The size-processed liposome suspension may be readily sterilized by passage through a sterilizing membrane having a particle discrimination size of about 0.4 μm, such as a conventional 0.45 μm depth membrane filter. The liposomes are stable in lyophilized form and can be reconstitued shortly before use by taking up in water.

According to the method of the invention the vesicles are loaded with biopolymeric substances which are virions, enzymes, growth factors, cytokines, proenzymes, co-factors, submicron particles such as ribosomes, hepatitis B surface antigen, vaccine, oligo- and polynucleotides, antibodies, or antigenic substances. In particular enzymes or proenzymes as well as co-factors are those which are naturally occurring in the blood stream. These substances are, for example, those which are functional in the blood clotting cascade such as factor VII, VIII, IX, X, XIII, fibriongen, prothrombin and/or thrombin. Also with substances having fibrinolytic activities such as plasmin, plasminogen or substances which are active in the complement system and/or are related with other functions in the immune system (humoral or tissue bound) the liposomes can be loaded according to the method of the invention. The biopolymeric substances may be derived from any source such as aninmal or human tissue culture, microorganisms, or transformed microorganisms, blood, blood plasma, or other body fluids.

Suitable lipids for forming liposomes are described above but particularly preferred are phospholidids such as dimirystoylphosphatidylcholine (DMPC) and/or dimirystoylphosphatidylglycerol (DMPG), egg and soybean derived phospholipids as obtained after partial or complete purification, directly or followed by partial or complete hydrogenation.

In general the method of the present invention (method A in FIG. 1) comprises the steps:

a) mixing amphiphatic substances, such as lipids suitable for forming vesicles in water-immiscible organic solvents b) removing of the solvent in presence of a solid support, alternatively, dried amphiphatic substances or mixtures thereof can be used in any form (powder, granular, etc.) directly, c) taking up the product of step b) into a solution of the biopolymeric substances in a physiologically compatible solution d) adding an organic solvent having solubilizing or dispersing properties, as well as e) drying the fraction obtained in step d) under conditions retaining the function of the biopolymeric substances.

This method is in the following referred to as a method A.

BRIEF DESCRIPTION OF THE DRAWINGS

FIGS. 8 and 9 are graphs recording the results of Factor VIII chromogenic assay over time.

Figure 1:
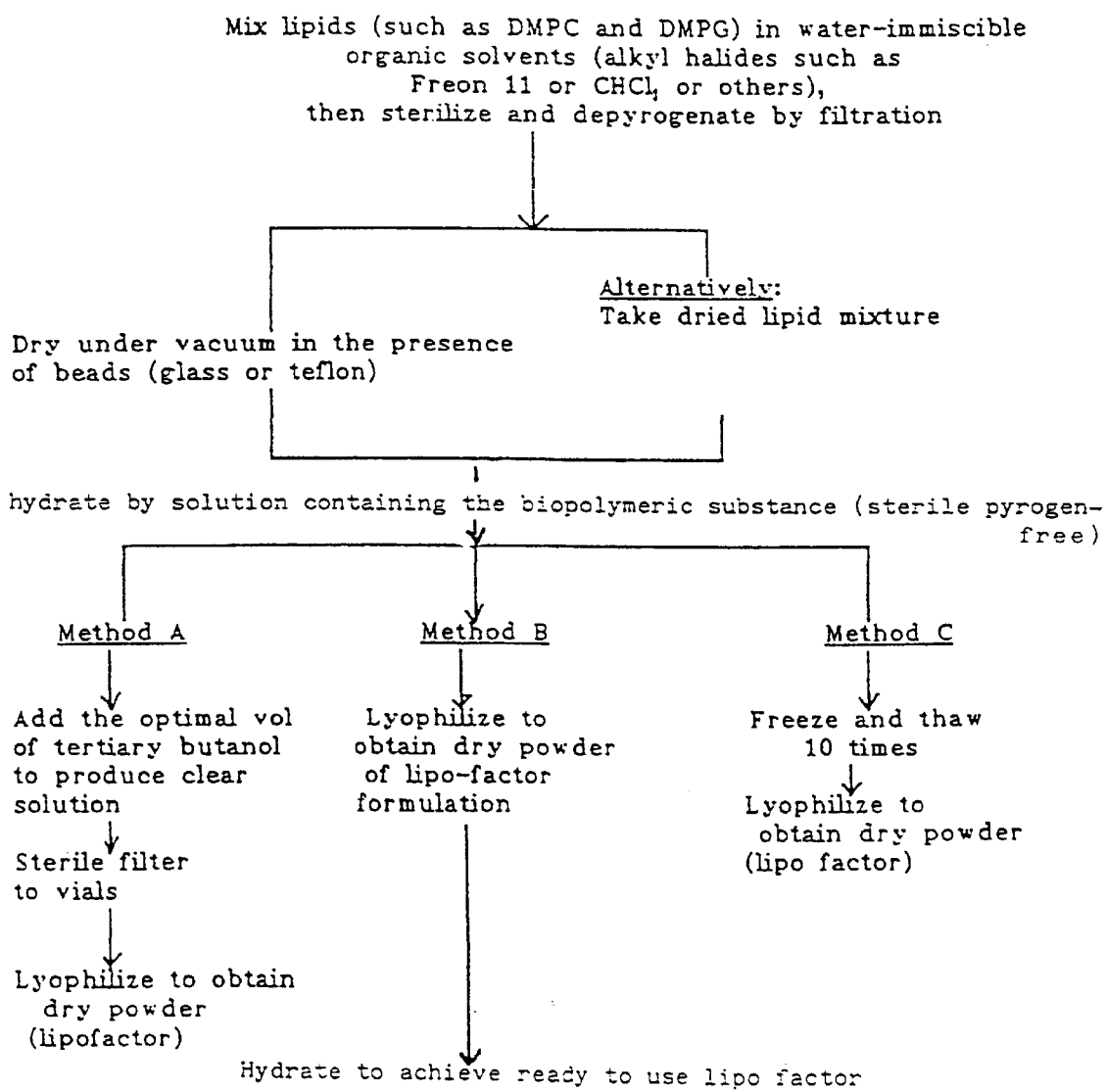
FIG. 1 is a schematic outline of the preparation of anti-HBV vaccine using methods A, B and C.

According to step a) of method A amphiphatic substances suitable for forming vesicles as mentioned above are mixed in a water-immiscible organic solvent. Preferably, the water-immiscible organic solvent is a polar-protic solvent such as fluorinated hydrocarbons, chlorinated hydrocarbons and the like.

In step b) of the method of the invention the solvent is removed in presence of a solid support. Preferably, the solid support is an inert organic or inorganic material having a bead-like structure. Preferably, the material of the inorganic support material is glass and the organic material can be teflon or other similar polymers.

The step c) of method A of the invention is for taking up the product of step b) into a solution of the substances to be encapsulated in a physiologically compatible solution. Preferably, the physiological compatible solution is equivalent to a sodium chloride solution up to about 1.5% by weight. It is also possible to use other salts as long as they are physiologically compatible e.g. as cryoprotectant e. g., sugars and/or amino acids. Preferably, lactose, sucrose or trehalose is used as a cryoprotectant.

Optionally, between step a) and b) a step of virus inactivation, sterilizing, depyrogenating, filtering the fraction or the like of step a) can be provided. This might be advantageous in order to have a pharmaceutically acceptable solution at an early stage of the preparation.

The step d) of the method of the invention is adding an organic solvent having solubilizing or dispersing properties.

Preferably, this organic solvent is an organic polar-protic solvent miscible with water. Preferably, lower aliphatic alcohols having 1 to 5 carbon atoms in the alkyl chain can be used. Very preferred is the use of tertiary butanol (tert.-butanol). It is unterstood by the skilled person that the amount of organic polar-protic solvent miscible with water is strongly dependend on its interference with the substance to be loaded to the liposomes. For example, if a protein is to be loaded the upper limit is set by the amount of solvent by which the effectivity of the protein becomes effected. This may strongly vary with the nature of the substance to be loaded. For example, if factor IX which is a clotting factor is to be loaded an amount of about 30% of tert.-butanol is tolerable, whereas, factor VIII is much more sensitive to the impact of tert.-butanol. In this case an amount of less than 10% of tert.-butanol is preferred. The percentage of tert.-butanol in these examples is based on percent by volume calculated for final concentration.

Optionally, subsequent to step d), virus inactivation sterilizing and/or portioning of the fraction yielded after step d) can be carried out.

The step e) of the present invention is drying the fraction obtained in step d) under conditions retaining the function of the substance to be loaded. A preferred method for drying the mixture is lyophilization. The lyophilization may be carried out in presence of a cryoprotectant, for example, lactose or other saccharides or amino acids. Alternatively, evaporation or spray-drying can be used.

The dried residue can then be taken up in an aqueous medium prior to use. After taking up of the solid it forms a dispersion of the respective liposomes. The aqueous medium contains preferably a saline solution and the dispersion formed can optionally passed through a suitable filter in order to down size the liposomes if necessary. Preferably, the liposomes have a size of 0.02 to 5 $\mu$m, more preferably in the range of $\leq 0.4$ $\mu$m.

The liposomes obtainable by the method A of the invention show high loading of the biopolymeric substances.

According to the invention a formulation is claimed comprising biopolymeric substances such as enzymes, proenzymes, co-factors, antigenes and/or antibodies functional in human, biochemical, or physiological systems obtainable by the method of the invention. The formulation comprises liposomes having loaded the substances as mentioned above which are, for example, naturally occurring in the blood stream such as those being functional in the blood clotting cascade such as factor VII, factor VIII, factor IX, factor X, fibrinogen, prothrombin, and/or thrombin or having fibrinolytic activities such as plasminogen, plasmin or which are active in the complement systems and/or are related with other functions in the immune system (humoral or tissue bound). The latter can be antigens or antibodies. The formulation of the invention can as well be an intermediate product obtainable by isolation of either fraction of step c) or d) of the method A. According to the invention the formulation of the invention also comprises an aqueous dispersion obtainable after taking up the product of step e) of method A in water in form of a dispersion (liposomes in aqueous medium).

The formulation of the invention can be used to prepare a medicament comprising the formulation and/or additionally other pharmaceutically active substances and vehicles and/or adjuvants and vaccines.

Alternatively, the formulation of the invention is also obtainable by the following methods which are referred to as method B, C and D.

Method B

This method comprises also the steps a), b) and c) of the method A. However, step d) and on of method A are omitted.

Method C

In method C step d) of method A is replaced by a freeze and thaw cycle which has to be repeated at least two times. This step is well-known in prior art to produce liposomes.

Method D

Method D excludes the use of any osmotic component. In method D the steps of preparation of vesicles, admixing a substantially salt free solution of the substances to be loaded and co-drying of the fractions thus obtained is involved.

Method E

Method E is simpler than methods A–D described above. It requires dissolving the compounds used for liposome preparation (lipids antioxidants, etc.) in a polar-protic water miscible solvent such as tert.-butanol. This solution is then mixed with an aqueous solution or dispersion containing the active agent which can be an antigen, enzyme, proenzyme, clotting factor, oligo or polynucleotides, etc. The mixing is performed at the optimum volume ratio required to maintain the biological and pharmacological activity of the agent. The mixture is then lyophilized in the presence or absence of cryoprotectant. Rehydration is required before the use of the liposomal formulation. These liposomes are multi-lamellar, their downsizing is achieved by one of the methods described above (see FIG. 3).

The methods A to E show in an advantageous manner high loading of the respective substances. Especially, methods A, D and E are suitable to incorporate enzymes, proenzymes and/or co-factors naturally occurring in the blood stream such as factor VII, VIII, IX, XIII playing an important role in the blood clotting cascade.

Figure 4:
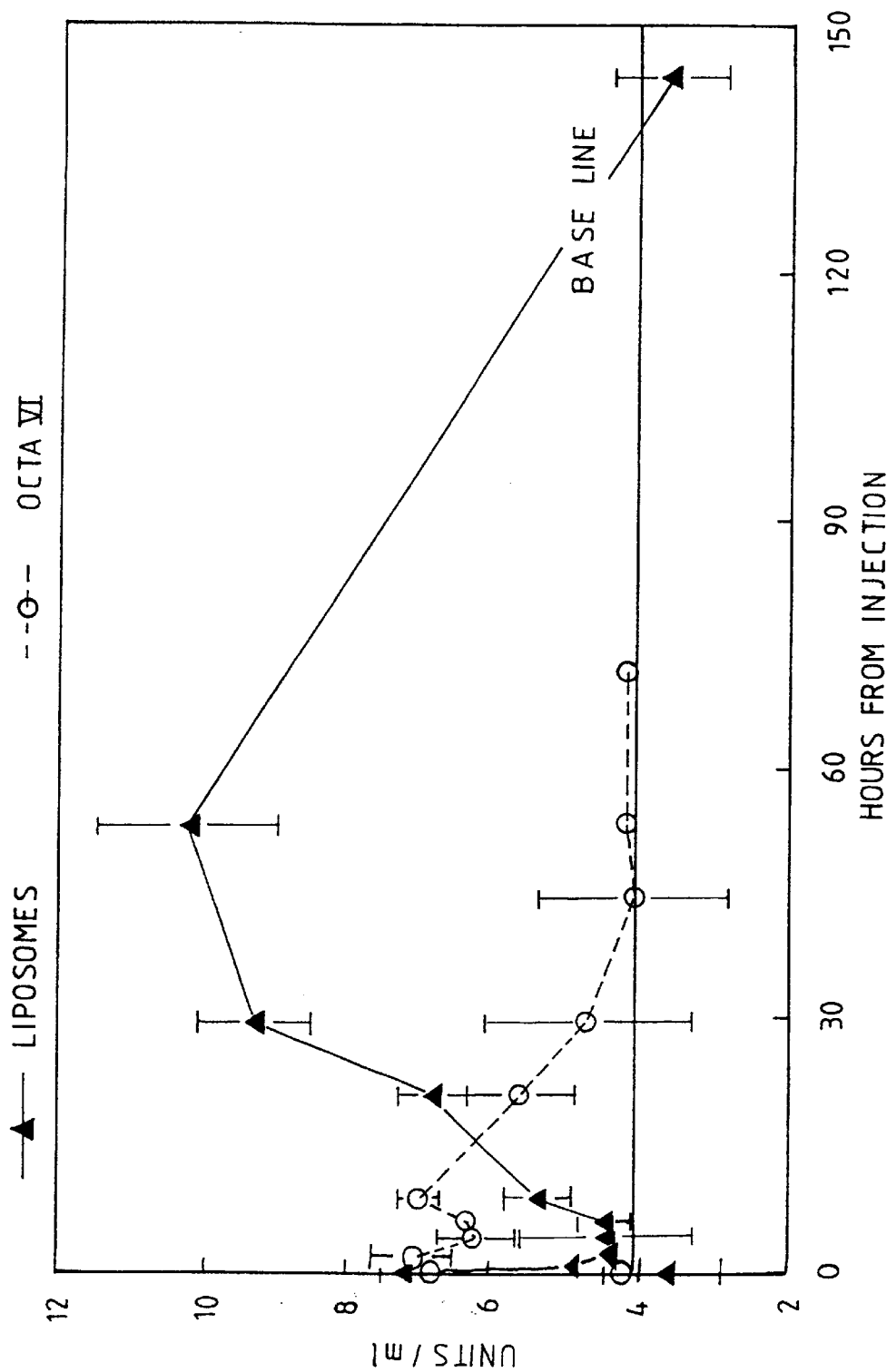
FIG. 4 is a chart showing average results and standard deviation of factor VIII clotting activity.
Figure 6:
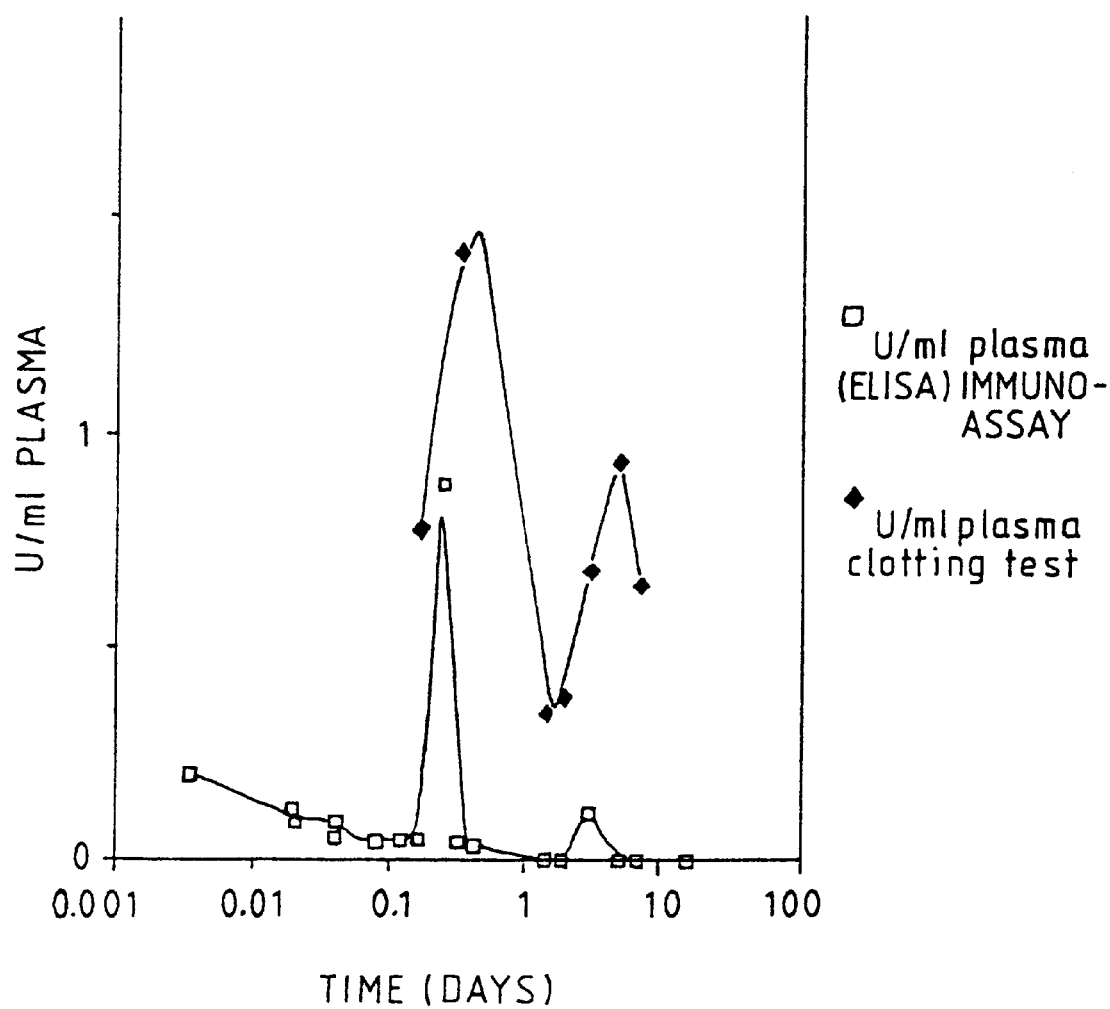

The formulation of the present invention in form of a medicament has an advantageous scope since the lidosomes loaded with e. g. clotting factors surprisingly show not only a sustained release of the drug but also a very low immunore-activity as well as an unexpected pharmacokinetic behaviour. This may be due to an accumalation of the liposomes in an organ, probably in the liver, from which organ the respective clotting factor is released during an unexpected long duration and quantity. The low antigenicity and recognition by the inhibitors of the protein-like substances loaded in the liposomes obtainable by the method A–E may be due to to its "masking" in the liposomes. The unexpected pharmacokinetics are shown in FIGS. 4 and 6 in which the biphasic release of the active factors is shown.

Thus, also a method of treating diseases by administering an effective amount of the medicament according to the present invention is claimed. The method of treating comprises the steps of an oral, buccal, intravenous, topical, intraperitoneal, pulmonary, or rectal administration of a medicament of the invention. If, for example, bleeding disorders must be treated, liposomes loaded with the respective factors are to be formed and administered to the patient. Preferably, this happens intravenously.

It is understood by the skilled person that the dosage of the medicament of the invention is depending on the concentration of the effective biopolymeric substances as well as their efficiency.

Preferably, a dosage up to 2.000 mg/liposomes lipid per kg body weight are administered in the patients wherein the active factors in the liposomes are loaded with an efficiency of higher than 50% based on the total activity used for preparing the loaded liposomes.

The accurate dosage can vary dramatically. The variation, however, depends on e. g. the type and efficacy of the substance encapsulated in the liposomes, the efficiency of the encapsulation reaction itself (being high with the method of the invention), the kind of administration and the like. The respective parameters can be easily optimized by the person skilled in the art and can be regarded as being routine experiments.

The following more specific embodiments explain the invention further:

There are two main types of vaccines against hepatitis B virus (HBV), both of which are aqueous dispersions based on 22 nm particles of hepatitis B virus surface antigen (HBsAg) as an immunogen and on aluminum hydroxide (alum) as adjuvant. A first vaccine is based on HBsAg particles obtained from human plasma of chronic HBV carriers. A second vaccine is based on HBsAg particles produced by yeast using recombinant DNA technology. The vaccine is safe and efficacious in preventing the disease in most humans, except certain groups of low responders and nonresponders. However, the vaccine looses its immunogenicity upon unoptimal storage conditions, such as freezing and heating beyond 8° C. In fact, these aluminum hydroxide-based vaccines are labeled with warnings such as "Do not freeze since freezing destroys potency" and "Store at 2–8° C." and "Storage above or below recommended temperature may reduce potency" (Recombivax HB®, MSD). This instability is related to the aluminum hydroxide which serves as the adjuvant.

This invention is also directed to the development of an anti HBV liposomal vaccine which is stable under a broad range of storage conditions, including freezing, freeze-drying and heating to room temperature. The vaccine is based on a recombinant HBsAg as antigene and on liposomes as adjuvant and stabilizer. Two preferred methods for producing this liposomal vaccine are described.

Seroconversion in mice clearly demonstrated that the liposomal vaccines of the instant invention are efficacious against HBV and produce a protecting titer of HBs antibodies, yielding at least an equivalent or better serum level of anti HBsAg antibodies to that obtaines using fresh vaccine based on alum as adjuvant. It is clear that applicants' liposomal vaccines retain their immunogenic activity under suboptimal conditions.

Method of Preparing Anti-HBV Liposomal Vaccine Based on Preformed Multilamellaar Vesicles (Methods A, B and C)

FIG. 1 outlines schematically the preparation of anti-HBV vaccine using methods A, B, C and E. In these methods the liposomes are produced during the hydration process.

It was desireable to develop a vaccine against HBV in the form of dry powder which should be at least as efficacious as currently available vaccines and the stability of which should be higher than current vaccines especially under extreme storage conditions.

The vaccine which was produced is based on liposomes as adjuvant and contain HBsAg particles as the immunogenic antigene. Any HBsAg may be used as immunogenic antigen to produce an anti HBV liposomal vaccine using the methods described in this application, and either the intact HBsAg particles or components of it may be employed. The HBsAg used herein is produced by recombinant methods in CHO cells as described in WO 90/10058. It is composed of three polypeptides—S, PreS1, PreS2 (in weight ratios of 78:8:14, respectively). Approximately, 30% of its weight is phospholipids and approximately 10% is cholesterol (see FIG. 1). Phosphatidylcholine is the main phospholipid; for the exact composition see Table 1.

TABLE 1

Phospholipid composition (%) of the hepatitis B virus antigene used

|  | PC | SPM | PI | PE | Lyso-PC | PS |
|---|---|---|---|---|---|---|
| Batch A | 63.4 | 11.3 | 8.7 | 7.0 | 5.3 | 4.3 |
| Batch B | 58.0 | 17.6 | 6.5 | 5.2 | 7.4 | 5.3 |

Abbreviations
PI = phosphatidylinositol
PC = phosphatidylcholine
SPM = sphingomyelin
PE = phosphatidylethanolamine
Lyso-PC = lyso-phosphatidylcholine
PS = phosphatidylserine The selection of phospholipids for the lipsomal vaccine preparation is based on two main parameters: (i) chemical stability; (ii) uptake by macrophages. Surprisingly, the selection of dimyristoyl phosphatidylcholine (DMPC) and dimyristoyl phosphatidylglycerol (DMPG) as the raw material for liposome preparation was advantageous. These disaturated phospholipids are not susceptible to various oxidation processes. Their gel to liquid crystalline phase transition ($T_m$) is 24° C., and therefore at 37° C. the lipids are in their liquid crystalline state, which is preferred for uptake by macrophages. The negative charge introduced by the DMPG also increases liposome uptake by macrophages which serve as antigene presenting cells. Large liposomes (multilamellar large vesicles) are advantageous due to their preferred uptake by the macrophages.

The general advantage of liposomes as adjuvants are known in the art including Gregoriadis, G. (1990) Immunology Today 11: 89–97 and Alving, C. in "Liposomes: Biophysics to Therapeutics" (1987), Marcel Dekker, N. Y. (Ostra, M. ed.) 195–218.

Methods of making lipsomes including multilamellar large vesicles are known in the art and are described in numerous publications, for example, the following major reviews which are hereby incorporated by reference New, F.R.C. ed. (1990) in "Liposomes", IRL, New York; Lichtenberg, D. and Barenholz, Y. (1988) in "Methods in Biochemical Analysis", 33: 337–462 (Glick, D. ed.).

Figure 2:
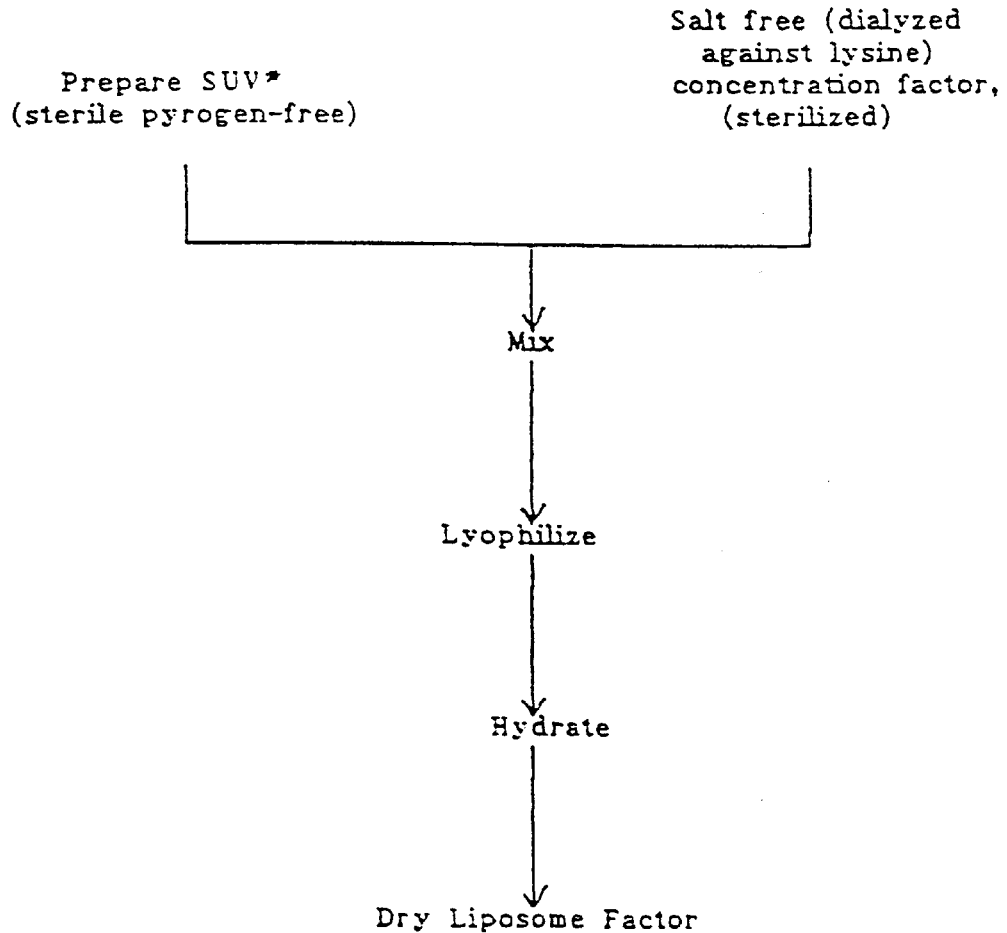
FIG. 2 is a schematic outline of the preparation of anti-HBV vaccine using method D showing good fit to a linear regression.
Figure 3:
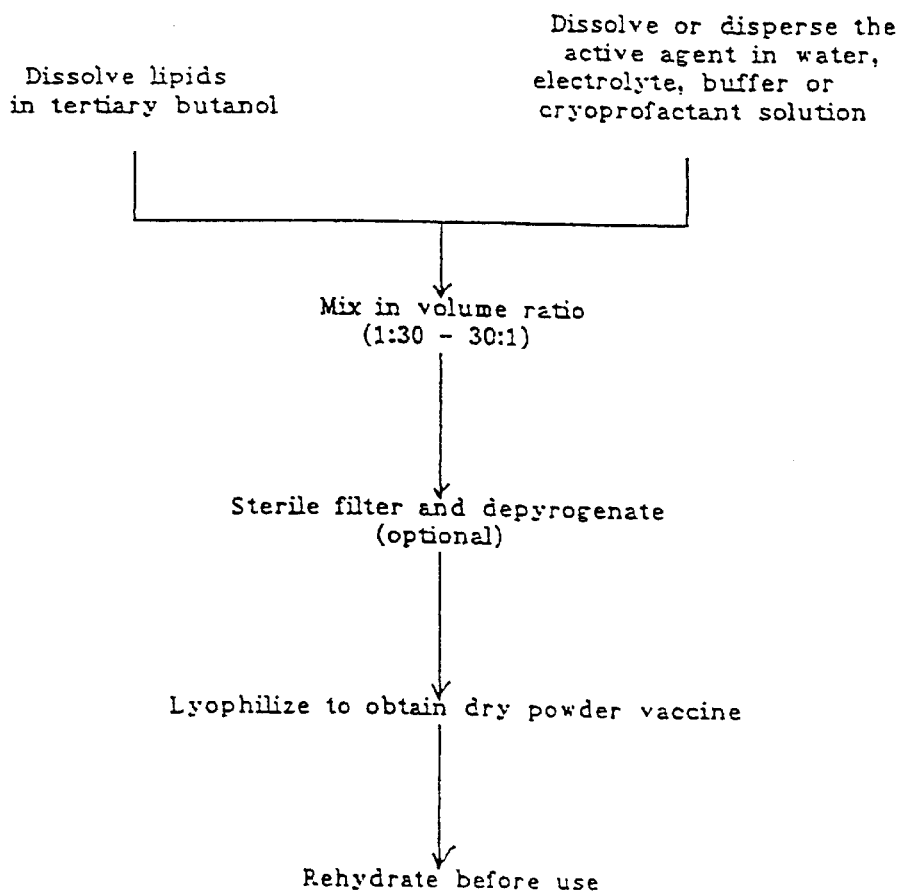
FIG. 3 is a schematic outline of the preparation of anti-HBV vaccine using method E.

Five methods A–E of preparing the liposomal vaccines based on multilamellar large vesicles (MLVs) were employed as described in detail in the following examples and in FIGS. 1, 2 and 3. Parameters that were tested and compared include the effect of lipid to antigen ratio, the extent of antigen exposure on the liposome surface, chemical and physical stability of the liposomal vaccine, comparison between various methods to prepare the liposomes on the above parameters, effect to freezing and thawing, lyophilization (freeze-drying) in the presence and absence of cryoprotectant (lactose) and the effect of an immunomodulator. Efficacy of the vaccine was determined by seroconversion in Balb/C mice 35 days after intra-peritoneal injection of the vaccine.

A summary of the results is presented in Table 2. These results showed that method A is preferred.

Richards, R. L. et al. (1989) vaccine 7: 506–512 disclosed a method of making liposomal malaria spurozite antigene which utilizes DMPC and DMPG but not alone; the liposomes were composed of DMPC, DMPG and cholesterol in molar ratios of 9:1:7.5. Lipid A and aluminum hydroxide were also present, and in the absence of these two compounds low immunogenicity resulted.

The liposomal vaccines described by Richards et al. 1989 was not prepared as dry powder but rather as aqueous dispersion.

TABLE 2

Summary of anti-HBs titer (mIU/ml) using the liposomal vaccine samples described in Examples 1–5

| Sample No. | Method of Preparation | $\mu$m HBsAg injected | | | |
|---|---|---|---|---|---|
|  |  | 0.09 | 0.27 | 0.81 | 2.5 |
| 1 | B | — | 249.4 ± 70.2 | 7,968.8 ± 1,510.3 | — |
| 2 | B | 128.7 ± 47.5 | 1,895.9 ± 139.0 | 2,797.1 ± 429.2 | 4,722.4 ± 636.0 |
| 3 | C | — | 199.2 ± 25.2 | 11,802.0 ± 3,748.1 | — |
| 4 | C | 80.3 ± 9.8 | 1,380.2 ± 254.5 | 563.7 ± 318.1 | 5,009.5 ± 918.6 |
| 5 | A | 102.2 ± 45.7 | 1,184.4 ± 676.7 | 2,209.4 ± 306.7 | 14,457.0 ± 5,337.8 |
| 6 | A | 72.3 ± 19.9 | — | — | — |
| 7 | A | 443.9 ± 37.4 | 2,613.8 ± 502.3 | 5,250.5 ± 1,276.3 | 8,367.5 ± 632.9 |
| 8 | E | 52.4 ± 18.6 | 426.7 ± 206.3 | 4,953.2 ± 1,211.5 | 6,692.0 ± 854.5 |
| 9 | E | 106.1 ± 16.5 | — | — | — |
| 10 | E | 193.3 ± 69.1 | 1,664.6 ± 392.8 | 2,701.4 ± 203.6 | — |
| 11 | E | 55.0 ± 17.3 | 895.9 ± 384.6 | 1,527.7 ± 166.6 | — |
| Control Alum-based vaccine | — | 40.0 ± 13.6 | 396.6 ± 73.1 | 6,749.3 ± 2,342.5 | 17,465.3 ± 2,967.0 |

Notes:
1) An anti HBsAg titer of 10 mIu/ml is considered to be a protecting dose against HBV infection.
2) The aluminum hydroxide (alum)-based vaccine used was the identical CHO vaccine prepared in a solution of aluminum hydroxide

EXAMPLE 1

Preparation of Samples of Anti-HBV Liposomal Vaccine Using Method A

The following samples of vaccine, designated (5), (6) and (7) were prepared using method A (see FIG. 1) amended as described below.

Sample (5): Liposomes containing HBsAg and "empty liposomes" were prepared as described for sample (1). Tert.-butanol was added (1:1 v/v) and the preparation was lyophilized. The resulting dry powder was reconstituted before use using sterile pyrogen-free double distilled water.

The loading of the antigen was 97% on average. The extent of HBsAg exposure on the liposome surface was determined by ELISA and found to be below detection. The size of liposomes was measured to be 4.5 µm, similar to the size of liposomes in other samples.

Immunization: Balb/c mice, six weeks old, were divided into four groups and vaccinated with doses as described for sample (2). The mice were bled after 35 days and the anti-HBs titer was determined and flund to be more than sufficient to protect against HBV infection. This titer was almost identical to that obtained after vaccination with the same HBsAg using aluminum hydroxide-based vaccine.

Sample (6): Liposomes containing HBsAg and "empty liposomes" were prepared as described for example (5). A group of seven Balb/c mice, six weeks old, were immunized with 0.09 µg HBsAg entrapped in liposomes which were diluted with "empty liposomes" and 0.9% NaCl. To the injeciton volume which was 0.5 ml of 1-palmitoyl-2-oleyl phosphatidylcholine (POPC) and dioleyl phosphatidylserine (DOPS) in a 7:3 molar ratio, liposomes containing the immuno-modulator muranyl tripeptide phosphatidylethanolamine (MTP-PE) at a level of 1 mg MTP-PE/1 kg mice were added. After 35 days anti-HBs was measured. There was no improvement above the antibody titer which was obtained by the same dose of liposomal vaccine not containing MTP-PE. (The use of MTP-PE as immuno-modulator is described for Herpes Simples Virus glycoprotein vaccine by Sanchez-Piscador et al., (1988) J. Immuno., 141: 1720–1727).

Sample (7): Liposomes containing HBsAg and "empty liposomes" were prepared as described for sample (5), except that the solution for lipid hydration also included 5% lactose as a cryoprotectant. The liposomes were frozen and dried. The dry powder obtained was reconstituted before use with sterile pyrogen-free double distilled water. The loading efficiency of HBsAg in the preparation, the size of the liposomes and the extent of HBsAg exposure on the liposomes were determined as described for sample (1). Similar results to those of sample (5) were obtained. The immunization efficacy of the liposomal vaccine was checked in Balb/c mice, as described for sample (2) and anti-HBs was measured 35 days after vaccination. In all cases a high titer of antibodes was obtained which can protect against infection by HBV. Comparison to the lactose-containing freeze-dried vaccine (sample (5)) clearly demonstrates that the lactose-containing vaccine was preferable for all doses of antigen used, except for the high dose (2.5 µg of protein).

EXAMPLE 2

Preparation of Anti-HBV Liposomal Vaccine Using Method B

The following samples of vaccine, designated samples (1) and (2), were prepared using method B (see FIG. 1) amended as described.

Sample (1): A mixture of the phospholipids dimyristoyl phosphatidyl choline (DMPC) and dimyristoyl phosphatidyl glycerol (DMPG) in a molar ratio of 9:1 respectively was dissovled in chloroform. The solvents were removed by flash evaporation under reduced pressure to complete dryness. The dried lipids were suspended in 0.9% NaCl solution containing HBsAg. The HBsAg: lipid (w/w) ratio, during liposomal preparation, was 0.0015. In this sample liposomes were obtained which loaded about 73% of the antigen used during lipid hydration; in similar samples using method B only 50–60% loading was achieved. The free (non-liposome associated) antigene was removed by ultra-centrifugation of the liposomal solution in 180,000 g for 60 minutes. The pellet was dispersed in sterile pyrogen-free 0.9% NaCl and was used for vaccination. Liposomes not containing antigen (referred to as "empty liposomes") were prepared by the same method to keep the lipid concentration of the samples identical.

Stability of the preparation: The physical stability of the liposomes was tested by measuring liposome size during storage using a Coulter Counter Model PCA-1. The mean diameter of fresh liposomes was 4.5 μm. The presence of antigen in the liposomes and their age up to 18 months had no significant effect on liposome size. The stability of liposomal components was also examined after one to three washes. Washing was performed by means of ultracentrifugation at 180,000 g for 60 minutes. After each wash the lipid: HBsAg (w/w) ratio in the liposome pellet was determined. It was found that this ratio remained constant troughout the washings and was the same as the ratio which was otained immediately after liposomal preparation; that is to say, there was no "leakage" of antigen from the liposomes. The extent of HBsAg exposure on the liposome surface was determined by ELISA using a standard commercial (Du Pont) kit, and was less than 5%.

Immunogenicity test: Salb/c mice, six weeks old, were used. The mice were divided into two groups of 8 mice. The first group was immunized by 0.27 μg of sample (1), the volume of intraperitoneal (i. p.) injection was 0.5 ml/mouse and included liposome entrapped HBsAg and "empty liposomes" in 0.9% NaCl; the two were mixed prior to injection in such a way that the same amount of lipids were injected to all mice. 35 days after immunization the mice were bled, and the antibody titer measured. It was found that all the mice that had been immunized by sample (1) developed protecting antibody titer at a level which should protect them from infection by HBV. These results were similar in their values to the results which had been obtained in the control group which included mice that had been immunized with the same free antigen (HBsAg) and aluminum hydroxide as the adjuvant.

Sample (2): A mixture of the phospholipids DMPC and DMPG in a molar ratio of 9:1 respectively was dissolved in chloroform. The solvents were removed by flash evaporation under reduced pressure to complete dryness. The dried lipids were dispersed in 0.9% NaCl solution containing HBsAg and 5% (by weight) of lactose. Liposomes (MLV) were produced by mechanical shaking, and were then lyophilized. The dried powder was reconstituted before use with double distilled sterile pyrogen free water. 75% of the input HBsAg was loaded. "Empty liposomes" were prepared under identical conditions to the above. The size of the liposomes (measured as described for sample (1)), was identical to sample (1). The process of freeze-drying did not affect liposome size. The extent of HBsAg exposure on the liposome surface was measured and found to be below detection.

Immunization: Balb/c mice, six weeks old, were divided into four groups of 8 mice. The mice were vaccinated with the liposomal preparation as described for sample (1). The following antigen doses (by protein weight) were injected: 0.09 μg, 0.27 μg, 0.81 μg, 2.5 μg. The mice were bled 35 days after vaccination and the titer of anti-HBs for this sample was determined. All mice developed protecting antibody titer.

EXAMPLE 3

Preparation of Anti-HBV Liposomal Vaccine Using Method C

The following samples of vaccine, designated samples (3) and (4) were prepared using method C (see FIG. 1) amended as described below.

Sample (3): Liposomes laoding HBsAg and "empty liposomes" were prepared as described for sample (1), followed by ten cycles of freezing at −180° C. and thawing at 37° C. The percentage of antigen loading in the liposomes was 81% on average. The free antigen which was not loaded was removed by ultracentrifugation (180,000 g for 60 minutes). Only the pellet was used as vaccine. The stability of liposomes was checked as described for sample (1) and the results of the examination were similar to those obtained for sample (1).

Immunization: Balb/c mice, six weeks old, were vaccinated by the liposomal vaccine against HBV. The test groups and experimental procedure in vivo was identical to that described for sample (1). The HBs antibody titer which had been developed after vaccination by the liposomal vaccine was always above the protecting level. The antibody titer which was obtained with this vaccine was the highest among the various liposomal preparations we tested. The titer was even higher than that obtained in the control group after vaccination by aluminum hydroxide-based vaccine containing the same HBsAg.

Sample (4): Liposomes loading HBsAg and "empty liposomes" were prepared as described for sample (3), with one difference in that the hydration of the lipids was performed in 5% lactose. The multilamellar liposomes which were formed were frozen and dried by lyophilization. The dry powder was stored at −21° C. untiluse. The size of the liposomes and the extent of HBsAg exposure on the liposome surface were tested as described for sample (1) and the results were identical to those obtained for sample (2).

The percentage of antigen loading in liposomes was 82% on average.

The immunization efficacy of this preparation was tested in Balb/c mice. The test groups and experimental procedure were the same as those described for sample (2). The results of this test demonstrate that the production of anti HBs antibodies in all antigen doses that were examined was above protecting level.

Comparing the efficacy of the dry liposomal preparation to the preparation which were stored as a dispersion (sample (3)) shows the superiority of the freeze-dried vaccine at low dose and of the vaccine stored as dispersion at high dose.

Comparison of Method A With Method C

Method A produces a high level of loading efficieny (entrapment) of the liposomes (about 97%) without the necessity for the cycles of freezing and thawing performed in method C. Since freezing and thawing is costly and inefficient at the industrial level, method E is a preferable method for industrial application. Thus, method E (which comprises the use of various mixtures of tert.-butanol and aqueous phase) is a preferred method for the production of immunologically active lyophilized anti-hepatitis B virus vaccine.

Comparison of Method B and C

Method C differs form method B in that method C comprises ten cycles of freezing and thawing which is a process known in the art for increasing encapsulation efficiency (antigen entrapment) of the liposomes (Lichtenberg, D. and Barenholz, Y. 1988). However, freezing and thawing may be costly and not cost-efficient for an industrial process.

EXAMPLE 4

Stability of Liposomal HBsAg Vaccine After Storage at Various Temperatures

As described above hepatitis vaccines known in the art use aluminum hydroxide as adjuvant and stabilizer. The disadvantage of the aluminum hydroxide-based vaccines is that they cannot be frozen nor can they be stored beyond 8° C. These vaccines thus have to be stored between 2–8° C. to maintain their efficacy.

There are three parameters to demonstrate stability of a vaccine under different conditions:

1. Efficiency (measure immunogenicity).
2. Chemical stability (measure hydrolysis of lipids; measure protein to lipid ratio).
3. Physical stability (measure size of particle).

The stability of the novel vaccine was tested after storage at three temperature (a) −20° c., (b) 2–6° C. and (c) room temperature.

The results obtained were as follows:

(a) The vaccine stored at −20 C. was effective after 1 month or more and was chemically and physically stable after 1.5 years or more.

(b) The vaccine stored at 2–6° C. was effective after 1 month or more and was chemically and physically stable after 1.5 years and more.

(c) The vaccine stored at room temperature was chemically and physically stable after 1.5 years or more.

These results demonstrate that the vaccine of the invention in form of liposoms is stable over a wide temperature range.

Since the current hepatitis vaccines lose their immunogenicity during freezing it is unexpected that the liposom-vaccine of the invention retains its activity both during the freezing step of the freeze drying process and also during storage of the vaccine below 0° C.

Thus, the advantage of HBV vaccine of the invention is evident. It does not need to be stored in a refrigerator and is not sensitive to freezing. The distribution of such a vaccine is greatly simplified especially in third world countries where the need for a vaccine against hepatitis B is greatest; additionally a vaccine which may be frozen aids distribution in countries such as Russia and China were the ambient temperature is often below freezing.

Applicants have thus produced a novel liposomal based HBsAg vaccine which is stable both below zero degrees and at room temperature, i. e. the vaccine may be stored under suboptimal conditions.

EXAMPLE 5

Loading of Factor VIII

Stability test: In order to load proteins in phospholipid membrane to form "cells" the interior of this compartment has to be isotonic to the solution outside.

A factor VIII preparation commercially available (Octa VI 250) was dissolved in 5 ml water (to obtain 50 units/ml), then dialyzed against various concentration of amino acids for 6 hours at 4° C. The dialyzed factor was then lyophilized for 20 hours. The samples were reconstituted first in water and then with saline to obtain 1:500 dilution.

Loading Experiments

A. Loading by Method E

In this preparation lipid solubilized in tert.-butanol is mixed with an aqueous solution of the factor to obtain an homogeneous solution. The solution is frozen and the solvent removed by lyophilization. Mulitlamellar vesicles loaded with Factor-IX are obtained by hydration of the dry mixture, firstly in small volume of bidistilled water, then stepwise with saline, until the final liposome concentration is reached. At this point the multlamellar vesicles can be sized by extrusion to obtain oligolamellar or small unilamellar vesicles.

Determination of Factor IX Activity

Factor IX activity was measured by a clotting assay. In this assay the percent of factor IX activity can be determined by the degree of correction obtained when a dilution of the tested sample is added to the factor IX Deficient Plasma (purchased from Baxter Diagnostics Inc.). The measuring instrument is called ACL-Automated Coagulation Laboratory from Instrumentation Labortory (Italy).

A calibration curve was first constructed for the clotting assay of factor IX, using appropriate dilutions of a stock solution of ca. 50 U/ml. FIG. 2 shows a good fit to a linear regression ($R^2$=0.989). Liposomes containing factor IX were pelleted by centrifugation in an Eppendorff centrifuge at 12,000 g for 10 min and the factor IX activitiy was determined in the supernatants and pellet. The pellet was solubilized prior analysis with Triton X-100. A concentration dependency on factor IX activity with Triton X100 was found. 1% Triton X100 (final concentration) caused a 50% loss of activity, while no loss was observed at 0.2%. In general, the total activity of the factor was recuperated, namely, the activity of the supernatants and pellet was always similar or even higher than the inital activity of the preparation. The loading efficiency was higher than 80%.

B. Loading by Method D

TABLE 4

Loading of FVIII by method D

| Fraction | Total Units | % of total |
|---|---|---|
| Liposomes associated FVIII activity | 103 | 73.5 |
| Free FVIII activity | 37 | 26.5 |

Rabbit experiment: In order to test factor VIII release from liposomes in the blood stream, rabbits were used as a model system.

The experiment was done on rabbits divided in 2 groups, weighing 3–3.5 kg. One group of rabbits was injected with 330 units of OctaVI and the other group of rabbits was injected with 330 units of factor VIII loaded in lipsomes. The liposomes were made from egg phosphatidylcholine (EPC) and were prepared by the SUV method. Percent of encapsulation was about 70%.

4 ml of blood samples were taken from the rabbits ears before the injection and at the following times after the injection: 30 minutes, 1 hr., 2 hrs, 4 hrs., 6 hrs., 21 hrs., 30 hrs., 45 hrs., 54 hrs., 72 hrs., and 144 hrs. Plasma was prepared from the blood samples and then frozen. At the end of the experiment, factor VIII activity was checked by one stage clotting assay.

The average results and standard deviation of factor VIII clotting activity of the rabbits that completed the experiment are presented in FIG. 4.

It can be seen that after injection of 330 units of free factor VIII activity raised from a basic level of 4 units/ml to 7 units/ml after 30 minutes and then decreased and reached the basic level after 45 hours. Factor VIII activity injected with liposome encapsulated factor VIII was first raised after 30 minutes, then decreased rapidly to the basic level. A second increase began 9 hours after injection, reached the top 54 hours after the injection and decrease to the basic level after 144 hours.

Based on these results, it seems that encapsulation of factor VIII in liposomes increased its half-life in rabbits.

EXAMPLE 6

Phospholipid and F VIII Formulation (method D)

A. Encapsulation of Monoclate® by Egg-PC

Monoclate® is an Armour formulation for F VIII that is purified by monoclonal antibody. The formulations contain F VIII:C only stabilized by large amount of albumin. The specific activity is very low, 5 units/mg protein. Encapsulation was done according the DRV method. Using ratio wt/wt mg of 107 and 214 phospholipid to 1 mg protein.

B. Octa VI With PL Supplemented With Cholesterol

| PC/Protein ratio | Egg PC 400 | Egg PC 250 | Egg PC + Cholesterol 217 |
|---|---|---|---|
| Unwashed liposome | 53 | 71 | 58 |
| Unwashed after blood filter supernatant | 55 | 67 | 28 |
| washed liposome | 17 | 6 | 12 |
|  | 28 | 26 | 34 |
| unwashed extracted with triton | 127 | 128 | 90 |
| washed extracted with triton | 98 | 89 | 75 |
| % loading * | 77 | 70 | 67 |

* Triton-X100 only partially dissolved the membrane containing cholesterol. Thus, the calculation was based partially on the theoretical F VIII input to the loading.

CONCLUSIONS

Ratio of 400:1 (wt/wt) lipid:protein is the best for Octa VI encapsulation in liposoomes.

Good encapsulation can be achieved also by using egg-PC supplemented with cholesterol. However, it cannot be recommended for chronic patients such as Haemophilia A, but can be used for acute patients.

EXAMPLE 7

The masking effect of liposomes loaded F VIII (Octa VI) is illustrated by performing an inhibitor test in vitro on patient plasma containing a high rate of inhibitors.

Inhibitors that occur in the plasma of hemophilics may be detected by Bethesda Inhibitory Test in which equal volumes of patient plasma (assuming there is no FVIII present) and normal plasma (1 unit of FVIII) is incubated at 37° C. Inhibitors are suspected if the coagulation time prolongs significantly when compared with that of mixtures of normal plasma and saline.

In the following experiment, for example, such patient plasma at various dilutions were incubated with standard pooled plasma (containing 100%=1 unit/mL of factor VIII). A dilution which yielded 50% decrease of factor VIII acitvity (expressed as residual concentration) of the incubated plasma is expressed quantitatively as Bethesda Inhibitor Units (BIU) of given plasma.

Figure 7:
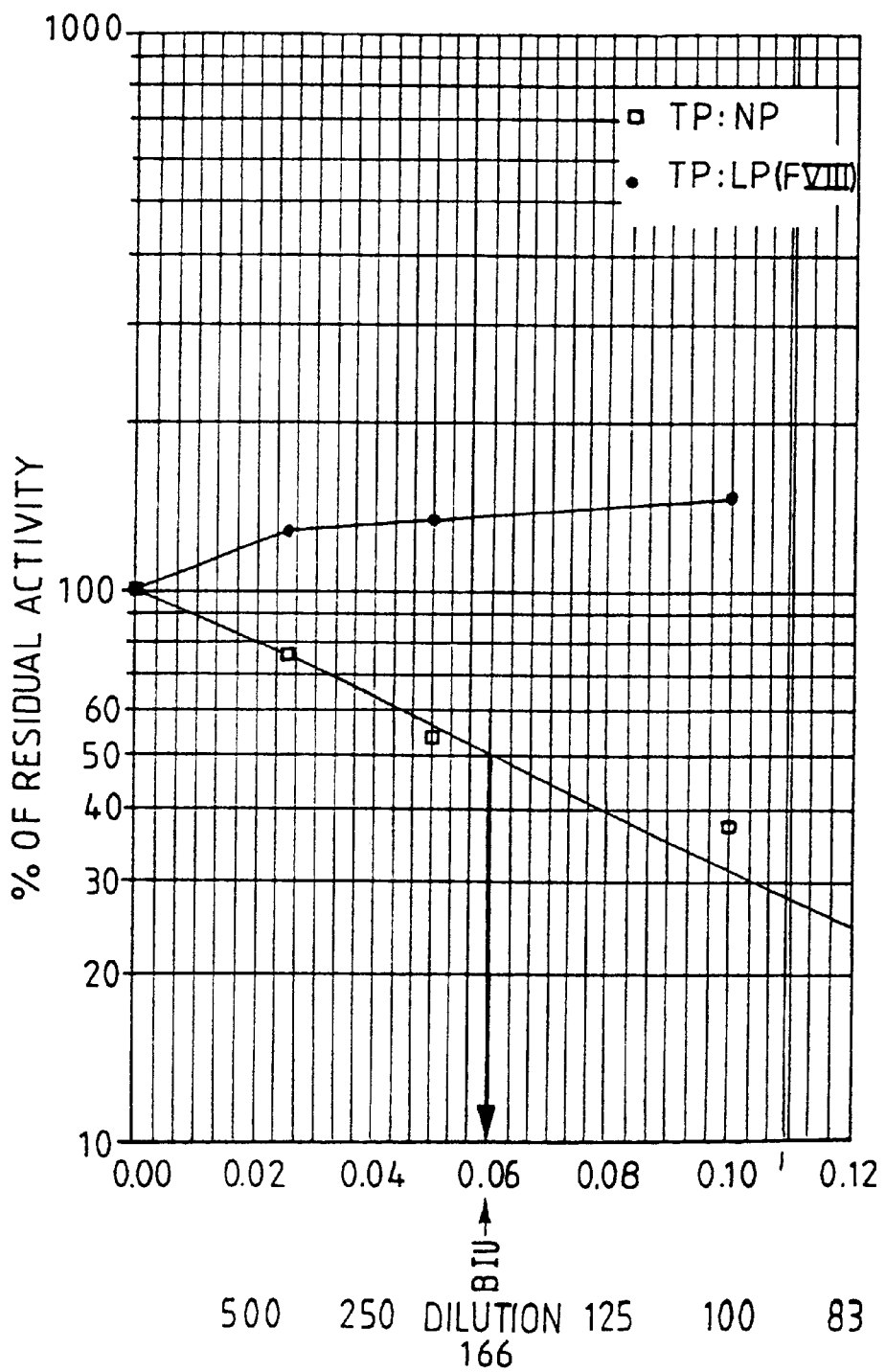
FIG. 7 records the ratio of factor VIII:C residual concentration.

FIG. 7 records the ratio of factor VIII: C residual concentration in the mixtures of patient plasma and normal plasma as compared to normal plasma mixed with saline. The results were plotted as percentages in semi-log numbers against the tested plasma dilution. A dilution refers to 50% of the original plasma is defined as the BIU per ml of a given plasma. In FIG. 1 the tested plasma has 160 BIU/mL. No inhibition was found (FIG. 1) when factors VIII:C loaded liposomes were incubated with tested plasma. In this experiment, factor VIII (OctaVI) loaded in liposomes were incubated for two hours at 37° C. with a given patient plasma dilution. The residual activity resulted from incubation with saline instead of patient plasma was considered as 100%.

EXAMPLE 8

A Comparison Between the Pharmacokinetics of Monoclate® and OctaVI Liposome Encapsualted FVIII Two Beagle dogs, a female a male, were injected with 900 units of liposome loaded FVIII. The male dog received liposomal loaded OctaVI (Octapharma AG), whereas, the female received capsulated MonoClate-P (Armour, USA). Blood samples were taken for 16 days from the injection time. The activity of factor VIII was monitored by a chromogenic assay.

As can be noticed in FIG. 8 and FIG. 9, the FVIII acitivity maintained for almost 3 weeks exhibiting a completely different pharmacokinetics as supposed from free FVIII (half life about 10–14 hours).

EXAMPLE 9

Measurement of the Level of Inhibitors

Rabbits tend to rapidly form inhibitor toward factor VIII.

Various dilutions of rabbit plasma were incubated for one hour at 37° C. with 5 units/ml of OctaVI. Activity was then tested by clotting assay.

Table 5

Inhibition units were calculated from ⅕ and ¹⁄₁₀ dilution of the rabbit's plasma in clotting assay buffer.

| Animal Treatment | Dilution 1/5 NIH Units | Dilution 1/10 NIH Units | Average ± SD |
|---|---|---|---|
| OctaVI | 13 | 19 | 16 ± 3 |
| Liposomal Octa VI | 0 | 0 | 0 |

The low immunogenicity of the phospholipid formulation may result from either both or each of the following mechanism:

a) OctaVI capsulated or rather embedded in a phospholipid bilayer membrane happened to be targeted toward an organ (presumably the liver) where it accumulated; then was released into the blood stream escaping recognition by the immune system or b) results may suggest that liposomal-FVIII presents a smaller target to the immune system. In other words, the lipsome is "masking" part of the factor antigenicity.

EXAMPLE 10

Preparation of Liposomes Containing Antihaemophilic Factor VIII

Liposome Preparation

The same procedure as in sample 3 was used to prepare liposomes containing factor VIII (OctaVI®, Octapharma. 60 to 90% loading efficiency was achieved.

EXAMPLE 11

Factor IX: dog experiment using method E

Two Beagle dogs were injected with 750 units of OctaNyne a commercial factor IX preparation (octapharma). The first dog was injected for the forth time with free OctaNyne whereas the second dog received capsulated FIX, this dog received factor for the first time (a "virgin" dog). OctaNyne formulation with lipsome was done according to method E and the capsulation was almost 100%, the amount of free factor was negligible.

Figure 5:
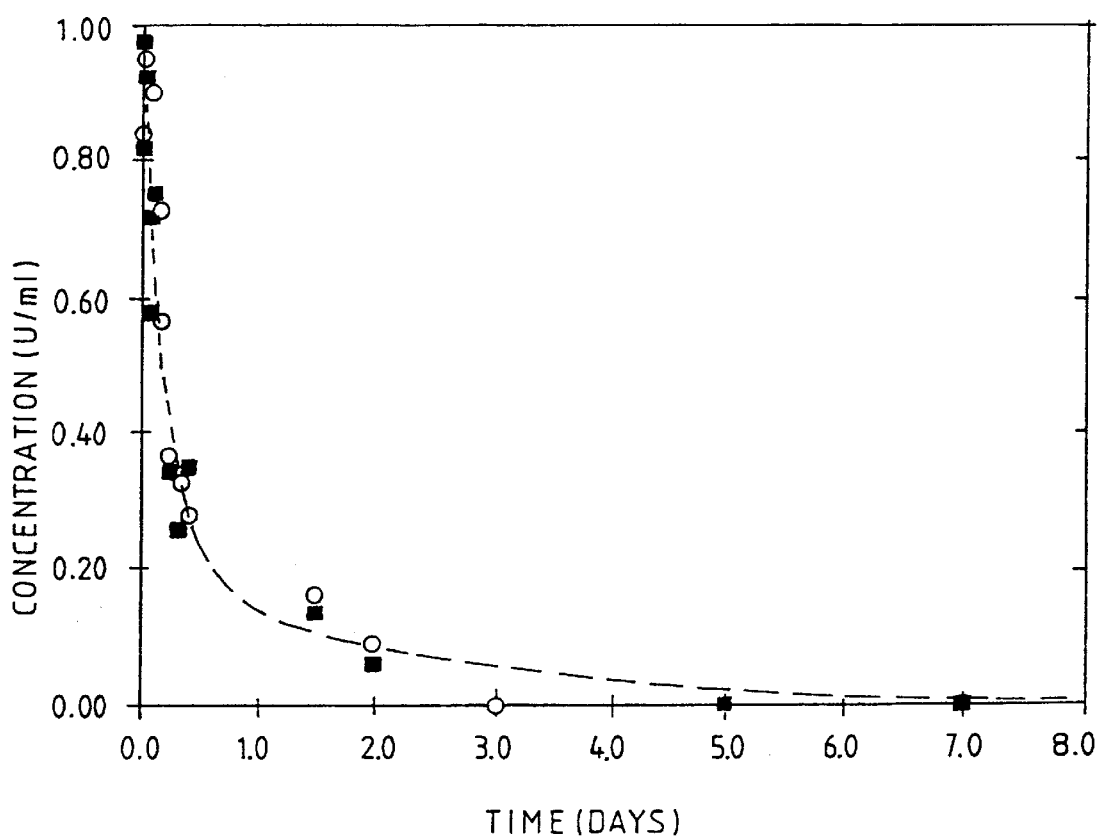
FIG. 5 and FIG. 6 are graphs recording the results of measuring concentration of free factor over time.

It can be see from the adjacent figures (FIGS. 5 and 6) that free factor has two half lifes. About 20% of the bolus have a half life of about 1.8 days whereas most of the bolus 80%, have a half life of 0.15 days.

On the other hand the liposome formulation has totally different kinds of behaviour. Analyzing the results received from the clotting assay shows that there are two peaks: one after 0.25 days and another after five days. The presence of factor IX in the blood as tested by an ELISA shows relatively low antigen activity, ⅕–¹⁄₁₀ of the activity recorded by the clotting assay in both methods. The activity peaks, however, happened at the same time.

The low activities recorded by the immune assay may be due to a "masking" effect created by the liposome in which additional blood protein were continuously embedded in the phospholipid bilayer during its circulation in the blood stream. An indication to this phenomena can be noticed in the following experiment.

The late peak that appears in this pharmacokinetic curve may suggest that the factor IX is accumulated in an organ (presumably the liver) and released slowly after a period of a few days.

EXAMPLE 12

The Immunogenic Masking Effect of Liposomes (in vitro experiment)

Large Scale Formulation of FVIII by Lecithin 3,000 units of factor VIII were capsulated by method D. The entire formulation was done in aseptic conditions in a class 100 clean room.

Results after reconstitution of the liposome were as follows:

TABLE 6

|  | Con. Units/ml | Volume | Total Units |
|---|---|---|---|
| Unwashed liposomes before B.F | 9.6 | 12.0 | 115.0 |
| Unwashed liposomes after B.F | 8.1 | 12.0 | 97.0 |
| Washed liposomes | 4.6 | 12.0 | 55.0 |
| Supernatant | 3.5 | 7.2 | 25.2 |
| Supernatant of washed liposomes | 0.9 | 7.2 | 6.5 |
| Unwashed extracted liposomes | 17.8 | 12.0 | 213.0 |
| Washed extracted | 11.4 | 12.0 | 136.8 |

Loading efficiency about 64%.

Separation of Free Factor VIII and Liposomes Encapsulated Factor VIII

1. Pass the liposome solution through a blood filter.
2. Transfer 1 ml into an 1.5 ml tube.
3. centrifuge the tube for 5 minutes, 14,000 g, at rooom temperature.

4. Transfer the supernatant into a new tube labeled "supernatant".

5. Add the same volume as the supernatant to the liposome pellet and resuspend carefully (avoid vortex).

6. Centrifuge again as in stage 4, transfer the supernatant into a clean 1.5 ml tube labeled "wash I".

7. Add the same volume as wash I to the liposome pellet and resusped carefully.

Measurement of Factor VIII Activity

1. Extraction and activity measurement of the whole liposome solution (containing the free factor VIII and the liposomes loaded factor VIII): Dilute x40 the liposomes solution into the assay buffer containing 1% of human serum albumin (HSA). Add Triton X-100 to 0.5%. Wait 10 minutes until the solution is cleared. Dilute at least 5 times the liposome extraction into assay buffer containing 1% HSA and measure factor VIII by one stage clotting assay.

2. Extraction and activity measurement of the washed liposomes: As described in stage 1.

3. Measure activity of supernatant and wash I fractions in one stage clotting assay (dilution x50–100 in the assay buffer containing 1% HSA).

4. Percent of loading=activity of washed liposomes extractions/activity of the whole liposomes solution.

Percentage of loading was 85%.

Immunoassay for the Detection of Factor VIII in Dog Plasma

Quantitative immunoassay in dog plasma is important for the detection of free factor VIII in normal dogs and the ratio of the clotting assay and factor VIIIAg can reflect on the presentation of FVIII antigen to immune system of dogs.

ELISA Assay Procedure

Microtitrations plates were coated by incubation on at 20° C. with 1/500 dilution (in PBS) of monoclonal anti FVIIIAg (York). Blocking was done at room temperature for 2 hours ⅕ dog plasma in PBS Tween 20 (0.05%). FVIII calibration curve was done by diluting OCTAVI in dog plasma. Samples were incubated for 2 hours at room temperature. Goat anti FVIII related antigen (ATAB) was used as a second antibody. A dilution of 1/500 in PBS was incubated for 2 hours at room temperature. The reaction was developed for 5 min after addition of the conjugate and the substrate.

Conclusion

A quantitative ELISA can detect FVIIIAg 2–70% clotting activity in dog plasma, which is about 0.02–0.7 units of human FVIII per ml (sensitivity of few nanogram).

Determination of the Ratio FVIII:C/FVIIIAg in Liposomes in Dog Serum

Assay procedure: Liposomes prepared by method D with various ratio of phospholipid (protein/lecithin 1/1,000 1/400 1/100 was washed from the free non loaded FVIII to measure the activity of the membrane embedded FVIII. The clotting activitiy was tested by a one step clotting test and the immune reactivity was tested by ELISA. The liposome was then lysed by Triton-100 to measure the combined activity of the loaded (embedded+encapsulated) FVIII.

TABLE 7

Effect of phospholipid on the encapsulation and masking the FVIII immunoreactivity in dog plasma.

|  | ratio protein/lipid | clotting activity | Immune-reactivity | ratio FVIII/FVIIIAg | % loading |
|---|---|---|---|---|---|
| Washed liposomes | 1/100 | 13.6 | 3.176 | 4.28 | 55 |
| supernatant | 1/100 | 30 | 39.15 | 0.766 |  |
| Washed liposomes | 1/400 | 4.9 | 0 | >>>>>> | 82 |
| supernatant | 1/400 | 5.0 | 5.1 | 0.99 |  |
| Washed liposomes | 1/1000 | 1.85 | 0 | >>>>>> | 73 |
| supernatant | 1/1000 | 1.05 | 0.88 | 1.19 |  |

Conclusion: The best loading and antigen masking was achieved at a ratio of 1/400 protein to phospholipd.

What is claimed is:

1. A method for effecting a dry product that forms liposomes, upon hydration, comprising the sequential steps of:
   i) combining one or more dry, liposome-forming lipids with a physiologically compatible solution of a biopolymeric substance functional in humans selected from the group consisting of enzymes, proenzymes, cofactors, virions, growth factors, cytokines, ribosomes, hepatitis-B surface antigen, oligo- and polynucleotides, antibodies, antigens and combinations thereof, effecting a lipid-containing mixture;
   ii) combining said mixture with an organic polar-protic solvent miscible with water, effecting an organic solvent fraction; and
   iii) lyophilizing said organic solvent fraction, which effects said dry product; whereby said dry product has capacity to form, upon hydration, liposomes of said biopolymeric substance encapsulated within said liposome-forming lipids.

2. The method of claim 1 whereby said dry liposome-forming lipids are obtained by mixing one or more liposome-forming lipids in a water-immiscible organic solvent, effecting a lipid/solvent mixture, followed by removing the organic solvent from the lipid/solvent mixture in the presence of a solid support.

3. The method of claim 2 whereby said lipid/solvent mixture is subjected, prior to removing the organic solvent, to a step selected from the group consisting of sterilization, depyrogenation, virus inactivation, filtration, and combinations, thereof.

4. The method of claim 1 whereby said organic solvent fraction is subjected to a step selected from the group consisting of sterilization, virus inactivation, portionation, and combinations, thereof.

5. The method of claim 1 wherein said biopolymeric substances are selected for the group consisting of antibodies, enzymes, proenzymes, cofactors, and combinations, thereof, which naturally occur in humans.

6. The method of claim 5 wherein said enzymes, proenzymes, and cofactors are functional substances in the blood clotting cascade.

7. The method of claim 6 wherein said functional substances are selected from the group consisting of factor VII, VIII, IX, X, XIII, fibrinogen, prothrombin, thrombin, and combinations thereof.

8. The method of claim 1 wherein said enzymes, proenzymes, and cofactors are proteins having fibrinolytic activity.

9. The method of claim 8 wherein said proteins are selected from the group consisting of plasmin, plasminogen, and combinations, thereof.

10. The method of claim 5 wherein said antibodies, enzymes, proenzymes, cofactors, and combinations, thereof, are obtained from a source selected from the group consisting of animal tissue culture, human tissue culture, a microorganism, a transformed microorganism, blood, blood plasma, and a human or animal body fluid.

11. The method of claim 1 wherein said dry, liposome-forming lipids are phospholipids.

12. The method of claim 1 wherein said phospholipids are selected from the group consisting of egg phospholipids, soybean phospholipids, dimyristoyl phosphatidyl glycerol, and combinations, thereof.

13. The method according to claim 12 wherein the egg phospholipids are egg phosphatidyl choline.

14. The method of claim 2 wherein the organic polar protic solvent miscible with water is a lower aliphatic alcohol having 1–5 carbon atoms in the alkyl chain.

15. The method of claim 14 wherein the organic polar-protic solvent miscible with water is tert.-butanol.

16. The method of claim 2 wherein said solid support is an inert inorganic or organic material having a bead structure.

17. The method of claim 1 wherein the physiologically compatible solution has a sodium chloride concentration equivalent to about a 1.5 weight % sodium chloride solution.

18. The method of claim 1 further comprising the step of combining said dry fraction in aqueous medium, forming a dispersion or a paste.

19. The method of claim 1 whereby conditions of said drying step retains functionality of the biopolymeric substance, such that said functionality is retained, upon hydration, in said liposomes.

20. A product produced by the process of claim 1.
21. A product produced by the process of claim 2.
22. A product produced by the process of claim 3.
23. A product produced by the process of claim 4.
24. A product produced by the process of claim 10.
25. A product produced by the process of claim 11.
26. A product produced by the process of claim 14.
27. A product produced by the process of claim 18.
28. A product produced by the process of claim 19.

29. The product of claim 28 wherein the biopolymeric substances are selected from the group consisting of factor VII, VIII, IX, X, XIII fibrinogen, prothrombin, thrombin, plasminogen, and plasmin.

30. An intermediate produced by the method comprising combining one or more dry, liposome-forming lipids with a physiologically compatible solution of a biopolymeric substance functional in humans selected from the group consisting of enzymes, proenzymes, cofactors, virions, growth factors, cytokines, ribosomes, hepatitis-B surface antigen, oligo- and polynucleotides, antibodies, antigens and combinations thereof, effecting a lipid-containing mixture as said intermediate;

said lipid-containing mixture being useful in a method comprising:

combining said mixture with an organic polar-protic solvent miscible with water, effecting an organic solvent fraction;

lyophilizing said organic solvent fraction, which effects a dry product;

whereby said dry product has capacity to form, upon hydration, liposomes of said biopolymeric substance encapsulated within said liposome-forming lipids.

31. An intermediate produced by the method comprising:

combining one or more dry, liposome-forming lipids with a physiologically compatible solution of a biopolymeric substance functional in humans selected from the group consisting of enzymes, proenzymes, cofactors, virions, growth factors, cytokines, ribosomes, hepatitis-B surface antigen, oligo- and polynucleotides, antibodies, antigens and combinations thereof, effecting a lipid-containing mixture; and combining said mixture with an organic polar-protic solvent miscible with water, effecting an organic solvent fraction as said intermediate;

said organic solvent fraction being useful in a method comprising lyophilizing said organic solvent fraction, which effects a dry product;

whereby, said dry product has capacity to form, upon hydration, liposomes of said biopolymeric substance encapsulated within said liposome-forming lipids.

32. A medicament comprising the product of claim 20 in combination with a pharmacologically acceptable carrier or diluent.

33. A method of treating humans for deficiencies of biopolymeric substances functional in humans selected from the group consisting of enzymes, proenzymes, cofactors, virions, growth factors, cytokines, ribosomes, hepatitis-B surface antigen, oligo- and polynucleotides, antibodies, antigens or combinations thereof comprising administering an effective amount of the medicament of claim 32.

34. The method of claim 33 wherein a dosage up to about 2 g liposomal phospholipid per kg body weight is administered.

35. The method of claim 33 for treating deficiencies of factor VII, factor IX, or a combination, thereof, wherein the medicament comprises liposomes loaded with F VIII, F IX, or a combination thereof.

36. The method of claim 1 wherein, upon reconstituting with water, the dried powder effects liposomes that have a selective size distribution no greater than 0.4 μm.

* * * * *